US008637240B2

(12) United States Patent
Tian et al.

(10) Patent No.: US 8,637,240 B2
(45) Date of Patent: Jan. 28, 2014

(54) USE OF GENE EXPRESSION SIGNATURES TO DETERMINE CANCER GRADE

(75) Inventors: Qiang Tian, Seattle, WA (US); Greg D. Foltz, Seattle, WA (US); Leroy Hood, Seattle, WA (US); Xiaowei Yan, Bellevue, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 12/892,710

(22) Filed: Sep. 28, 2010

(65) Prior Publication Data

US 2011/0105340 A1 May 5, 2011

Related U.S. Application Data

(60) Provisional application No. 61/277,723, filed on Sep. 28, 2009.

(51) Int. Cl.
*C12Q 1/68* (2006.01)
*G01N 33/574* (2006.01)

(52) U.S. Cl.
USPC .......................................... 435/6.1; 435/7.23

(58) Field of Classification Search
None
See application file for complete search history.

(56) References Cited

U.S. PATENT DOCUMENTS

2009/0157326 A1   6/2009  Dai et al.

FOREIGN PATENT DOCUMENTS

WO    WO-2006/131599    12/2006

OTHER PUBLICATIONS

Pusztai et al., Clinical trial design for microarray predictive marker discovery and assessment, Annals of Oncology 15: 1731-1737, 2004.*
Kroese et al., Genetic tests and their evaluation: Can we answer the key questions?, Genet Med 2004:6(6):475-480.*
Golub et al., Molecular Classification of Cancer: Class Discovery and Class Prediction by Gene Expression Monitoring, Science vol. 286 Oct. 15, 1999.*
Toren et al., CD133-Positive Hematopoietic Stem Cell "Sternness" Genes Contain Many Genes Mutated or Abnormally Expressed in Leukemia, Stem Cells 2005;23:1142-1153.*
Wright et al., Brca1 breast tumors contain distinct CD44+/CD24– and CD133+ cells with cancer stem cell characteristics, Breast Cancer Research 2008, 10:R10.*
Beier, CD133+and CD133– Glioblastoma-Derived Cancer Stem Cells Show Differential Growth Characteristics and Molecular Profiles, Cancer Res 2007; 67: (9). May 1, 2007, 4010-15.*
Beier et al., Cancer Research (2007) 67(9):4010-4015.
International Search Report and Written Opinion for PCT/US10/50564, mailed Dec. 16, 2010, 5 pages.
Ben-Porath et al., Nat. Genet. (2008) 40:499-507.
Liu et al., New England Journal of Medicine (2007) 356:217-226.
Setlur et al., Cancer Research (2007) 67:10296-10303.

* cited by examiner

*Primary Examiner* — Jim Ketter
*Assistant Examiner* — Reza Ghafoorian
(74) *Attorney, Agent, or Firm* — Morrison & Foerster LLP (57) ABSTRACT

Signatures indicative of cancer grades are based on over- and under-expression of 214 genes that characterize expression patterns in CD133+ cells.

5 Claims, 7 Drawing Sheets

USE OF GENE EXPRESSION SIGNATURES TO DETERMINE CANCER GRADE

CROSS-REFERENCE TO RELATED APPLICATIONS

This application claims priority from U.S. provisional application 61/277,723 filed 28 Sep. 2009. The contents of this document are incorporated herein by reference.

STATEMENT OF RIGHTS TO INVENTIONS MADE UNDER FEDERALLY SPONSORED RESEARCH

This work was supported in part by grants from the National Institutes of Health, grant numbers P01 DK53074, CA 119347 and P50 GM 076547. The U.S. government has certain rights in this invention.

TECHNICAL FIELD

The invention relates to gene expression patterns in various tumor tissues. Specifically, statistical methods are employed to compare signature levels of genes over- or under-expressed in CD133$^+$ cells with tissue samples from subjects. Tumors that exhibit patterns characteristic of CD133$^+$ cells are diagnostic of more aggressive tumors.

BACKGROUND ART

Cancer stem cells (CSC) are believed to be responsible for aggressive tumor growth. CSC have been reported to be characterized by the presence of the transmembrane protein CD133, although contradictory studies indicating that there may not be a one-to-one correlation between CD133$^+$ cells and aggressive tumor growth have also appeared. It has been shown clinically for breast cancer that determining the presence of CSC is useful in prognosis of outcome (Liu, R., et al., *New Engl. J. Med.* (2007) 356:217-226). Additional correlations have been found in glioblastoma multiforme (GBM) the most deadly form of brain cancer (Ben-Porath, I., et al., *Nat. Genet.* (2008)40:499-507).

All documents and citations listed herein are incorporated herein by reference in their entirety.

Because correlation of CD133$^+$ markers with tumor aggressiveness has not been demonstrated, alternative profiling methods have been designed. Various signatures have been proposed by, for example, OncoMed. The present invention provides profiles that are more successful in assessing prognosis.

DISCLOSURE OF THE INVENTION

The invention is directed to expression profiles characteristic of various stages or grades of tumor development. The present inventors have identified 89 genes whose expression is significantly elevated and 125 genes whose expression is significantly decreased in CD133$^+$ cells. As it has been determined herein that this signature correlates with the corresponding signature associated with stem cells, and relevance of the signature to cancer grade has been established.

Thus, in one aspect, the invention is directed to a method to assess the grade of a tumor in a subject, which method comprises assessing the collective level of expression of at least 10 genes in each of the overexpressed and/or underexpressed groups set forth in Table 1 and comparing the resulting collective levels with the collective levels with respect to over- or under-expression for each group of said 10 genes in CD133$^+$ vs. CD133$^-$ cells, whereby the degree of correlation between the collective expression levels in the tumor tissue and the collective levels in the same genes of Table 1 in CD133$^+$ vs. CD133$^-$ cells indicates the grade of said tumor.

More precise results may be obtained by increasing the number of genes that are included in the "up" and "down" panels to be assessed. A correlation of the expression pattern found in the tumor sample with the expression pattern found in CD133$^+$ cells is indicative of a more aggressive cancer.

BRIEF DESCRIPTION OF THE DRAWINGS

FIGS. 4a-b show signatures as compared to the expected up/down profiles in tissue samples isolated from patients with various grades of glioma.

MODES OF CARRYING OUT THE INVENTION

The invention relies on statistical treatment of expression patterns obtained using standard microarray technology. Expression patterns are compared to profiles associated with CD133$^-$ cells collectively using an unbiased algorithm developed by Setlur, S. R., et al., *Cancer Res.* (2007) 67:10296-10303. In this analysis, the entire profile of a given subset of genes (e.g., the CD133-up, or the CD133-down) is compared to the entire profile of the same set of genes in CD133$^-$ expression to denote collective under- and over-expression. Briefly, the Z score for each gene in the profile is calculated assuming that the expression has a normal distribution to minimize the noise arising from different expression profiles obtained across diverse platforms. The Z scores are then converted into corresponding P values. The negative logarithm values of the P values are designated as individual gene scores, and for a given subset of genes, the gene scores are summed to compute a score for the gene set. The significance of the gene set score is then determined by running $10^6$ iterations on randomly selected gene sets of the same size to calculate the P values which are used to generate heat maps.

A P value of zero represents an enrichment of over-expression of the genes in the gene set, a P value of one represents enrichment of under-expression and non-significant changes are represented by a P value of 0.5.

Table 1 below shows a list of the genes that are over- or under-expressed in CD133$^+$ cells as compared to CD133$^-$ cells, as determined in Preparation A below. Any subgroup of this may be used to obtain the relevant signature, although, of course, the greater the number of genes included, the more significant the results. Thus, subsets of 10, 20, 30, 40, etc., individual genes in each group up to the total in each group and all integers in between can be used in these analyses.

TABLE 1

List of 214 genes identified by subtractive analyses as GBM CD133 gene signature transcripts, with 89 elevated and 125 decreased in transcript levels in the CD133$^+$ cells.

List of 89 Genes Overexpressed in CD133$^+$ GBM Cells:

| | | |
|---|---|---|
| AKAP4 | 8852 | A kinase (PRKA) anchor protein 4 |
| ARHGAP11A | 9824 | Rho GTPase activating protein 11A |
| ASPM | 259266 | asp (abnormal spindle) homolog, microcephaly associated (*Drosophila*) |
| BARD1 | 580 | BRCA1 associated RING domain 1 |
| BIRC5 | 332 | baculoviral IAP repeat-containing 5 (survivin) |
| BRCA1 | 672 | breast cancer 1, early onset |
| C12orf32 | 83695 | chromosome 12 open reading frame 32 |
| C17orf80 | 55028 | chromosome 17 open reading frame 80 |
| C2orf48 | 348738 | chromosome 2 open reading frame 48 |
| C4orf21 | 55345 | chromosome 4 open reading frame 21 |
| CAPN14 | 440854 | calpain 14 |
| CASC5 | 57082 | cancer susceptibility candidate 5 |
| CCDC102A | 92922 | coiled-coil domain containing 102A |
| CCDC111 | 201973 | coiled-coil domain containing 111 |
| CCDC15 | 80071 | coiled-coil domain containing 15 |
| CDCA2 | 157313 | cell division cycle associated 2 |
| CDKN3 | 1033 | cyclin-dependent kinase inhibitor 3 (CDK2-associated dual specificity phosphatase) |
| CENPH | 64946 | centromere protein H |
| CENPK | 64105 | centromere protein K |
| CKAP2L | 150468 | cytoskeleton associated protein 2-like |
| CKS2 | 1164 | CDC28 protein kinase regulatory subunit 2 |
| CTNNAL1 | 8727 | catenin (cadherin-associated protein), alpha-like 1 |
| DHFR | 1719 | dihydrofolate reductase |
| DHX57 | 90957 | DEAH (Asp-Glu-Ala-Asp/His) box polypeptide 57 |
| DIAPH3 | 81624 | diaphanous homolog 3 (*Drosophila*) |
| DLGAP5 | 9787 | discs, large (*Drosophila*) homolog-associated protein 5 |
| DTL | 51514 | denticleless homolog (*Drosophila*) |
| DTYMK | 1841 | deoxythymidylate kinase (thymidylate kinase) |
| ECT2 | 1894 | epithelial cell transforming sequence 2 oncogene |
| ENAH | 55740 | enabled homolog (*Drosophila*) |
| FANCI | 55215 | Fanconi anemia, complementation group I |
| FBXO5 | 26271 | F-box protein 5 |
| GGH | 8836 | gamma-glutamyl hydrolase (conjugase, folylpolygammaglutamyl hydrolase) |

TABLE 1-continued

List of 214 genes identified by subtractive analyses as GBM CD133 gene signature transcripts, with 89 elevated and 125 decreased in transcript levels in the CD133$^+$ cells.

| | | |
|---|---|---|
| GINS2 | 51659 | GINS complex subunit 2 (Psf2 homolog) |
| GMNN | 51053 | geminin, DNA replication inhibitor |
| H2AFZ | 3015 | H2A histone family, member Z |
| HMGB2 | 3148 | high-mobility group box 2 |
| IFNA17 | 3451 | interferon, alpha 17 |
| IFNA4 | 3441 | interferon, alpha 4 |
| JAM2 | 58494 | junctional adhesion molecule 2 |
| KIAA0101 | 9768 | KIAA0101 |
| KIF11 | 3832 | kinesin family member 11 |
| KIF15 | 56992 | kinesin family member 15 |
| KIF2C | 11004 | kinesin family member 2C |
| KIF4A | 24137 | kinesin family member 4A |
| KNTC1 | 9735 | kinetochore associated 1 |
| LIG1 | 3978 | ligase I, DNA, ATP-dependent |
| LMAN1L | 79748 | lectin, mannose-binding, 1 like |
| LOC91431 | 91431 | prematurely terminated mRNA decay factor-like |
| MAD2L1 | 4085 | MAD2 mitotic arrest deficient-like 1 (yeast) |
| MCM2 | 4171 | minichromosome maintenance complex component 2 |
| MCM3 | 4172 | minichromosome maintenance complex component 3 |
| MELK | 9833 | maternal embryonic leucine zipper kinase |
| MND1 | 84057 | meiotic nuclear divisions 1 homolog (*S. cerevisiae*) |
| MORN2 | 378464 | MORN repeat containing 2 |
| NACA | 4666 | nascent polypeptide-associated complex alpha subunit |
| NCAPH | 23397 | non-SMC condensin I complex, subunit H |
| NDC80 | 10403 | NDC80 homolog, kinetochore complex component (*S. cerevisiae*) |
| NEK2 | 4751 | NIMA (never in mitosis gene a)-related kinase 2 |
| NMU | 10874 | neuromedin U |
| NUF2 | 83540 | NUF2, NDC80 kinetochore complex component, homolog (*S. cerevisiae*) |
| PBK | 55872 | PDZ binding kinase |
| PCNA | 5111 | proliferating cell nuclear antigen |
| POLQ | 10721 | polymerase (DNA directed), theta |
| PRIM1 | 5557 | primase, DNA, polypeptide 1 (49 kDa) |
| PROM1 | 8842 | prominin 1 |
| PSG5 | 5673 | pregnancy specific beta-1-glycoprotein 5 |
| PTTG1 | 9232 | pituitary tumor-transforming 1 |
| PTTG3 | 26255 | pituitary tumor-transforming 3 |
| PXMP2 | 5827 | peroxisomal membrane protein 2, 22 kDa |
| RAD51 | 5888 | RAD51 homolog (RecA homolog, *E. coli*) (*S. cerevisiae*) |
| RANBP1 | 5902 | RAN binding protein 1 |
| RRM2 | 6241 | ribonucleotide reductase M2 polypeptide |
| RTKN | 6242 | rhotekin |
| SGOL1 | 151648 | shugoshin-like 1 (*S. pombe*) |
| SLC2A11 | 66035 | solute carrier family 2 (facilitated glucose transporter), member 11 |
| SMC2 | 10592 | structural maintenance of chromosomes 2 |
| SNRPE | 6635 | small nuclear ribonucleoprotein polypeptide E |
| SYTL4 | 94121 | synaptotagmin-like 4 (granuphilin-a) |
| TIMELESS | 8914 | timeless homolog (*Drosophila*) |
| TM4SF1 | 4071 | transmembrane 4 L six family member 1 |
| TMEM106C | 79022 | transmembrane protein 106C |
| TOP2A | 7153 | topoisomerase (DNA) II alpha 170 kDa |
| TPX2 | 22974 | TPX2, microtubule-associated, homolog (*Xenopus laevis*) |
| TRIP13 | 9319 | thyroid hormone receptor interactor 13 |
| TROAP | 10024 | trophinin associated protein (tastin) |
| TTK | 7272 | TTK protein kinase |
| TYMS | 7298 | thymidylate synthetase |
| WDR34 | 89891 | WD repeat domain 34 |

List of 125 Genes Underexpressed in CD133$^+$ GBM Cells:

| | | |
|---|---|---|
| ABI3 | 51225 | ABI gene family, member 3 |
| ADAM8 | 101 | ADAM metallopeptidase domain 8 |
| ADARB2 | 105 | adenosine deaminase, RNA-specific, B2 (RED2 homolog rat) |

TABLE 1-continued

List of 214 genes identified by subtractive analyses as GBM CD133 gene signature transcripts, with 89 elevated and 125 decreased in transcript levels in the CD133+ cells.

| Symbol | ID | Description |
|---|---|---|
| ADCY7 | 113 | adenylate cyclase 7 |
| APBB1IP | 54518 | amyloid beta (A4) precursor protein-binding, family B, member 1 interacting protein |
| ARHGAP9 | 64333 | Rho GTPase activating protein 9 |
| ARHGDIB | 397 | Rho GDP dissociation inhibitor (GDI) beta |
| ATP10D | 57205 | ATPase, class V, type 10D |
| ATP8B4 | 79895 | ATPase, class I, type 8B, member 4 |
| BCL2 | 596 | B-cell CLL/lymphoma 2 |
| BEST1 | 7439 | bestrophin 1 |
| BIN1 | 274 | bridging integrator 1 |
| BIN2 | 51411 | bridging integrator 2 |
| BLNK | 29760 | B-cell linker |
| C10orf54 | 64115 | chromosome 10 open reading frame 54 |
| C1orf38 | 9473 | chromosome 1 open reading frame 38 |
| C20orf197 | 284756 | chromosome 20 open reading frame 197 |
| C9orf164 | 349236 | chromosome 9 open reading frame 164 |
| CAP2 | 10486 | CAP, adenylate cyclase-associated protein, 2 (yeast) |
| CCDC13 | 152206 | coiled-coil domain containing 13 |
| CCR5 | 1234 | chemokine (C-C motif) receptor 5 |
| CD28 | 940 | CD28 molecule |
| CD48 | 962 | CD48 molecule |
| CD52 | 1043 | CD52 molecule |
| CD53 | 963 | CD53 molecule |
| CD74 | 972 | CD74 molecule, major histocompatibility complex, class II invariant chain |
| CDC42EP2 | 10435 | CDC42 effector protein (Rho GTPase binding) 2 |
| CLEC7A | 64581 | C-type lectin domain family 7, member A |
| CPM | 1368 | carboxypeptidase M |
| CSF1R | 1436 | colony stimulating factor 1 receptor, formerly McDonough feline sarcoma viral (v-fms) oncogene homolog |
| CXCR6 | 10663 | chemokine (C-X-C motif) receptor 6 |
| CXorf21 | 80231 | chromosome X open reading frame 21 |
| DDX43 | 55510 | DEAD (Asp-Glu-Ala-Asp) box polypeptide 43 |
| DENND1C | 79958 | DENN/MADD domain containing 1C |
| DENND3 | 22898 | DENN/MADD domain containing 3 |
| DHRS9 | 10170 | dehydrogenase/reductase (SDR family) member 9 |
| DOCK2 | 1794 | dedicator of cytokinesis 2 |
| DOCK8 | 81704 | dedicator of cytokinesis 8 |
| DOK3 | 79930 | docking protein 3 |
| ECHDC3 | 79746 | enoyl Coenzyme A hydratase domain containing 3 |
| ELA3A | 10136 | elastase 3A, pancreatic |
| ELA3B | 23436 | elastase 3B, pancreatic |
| EVI2B | 2124 | ecotropic viral integration site 2B |
| FAM105A | 54491 | family with sequence similarity 105, member A |
| FAM123A | 219287 | family with sequence similarity 123A |
| FAM53B | 9679 | family with sequence similarity 53, member B |
| FTH1 | 2495 | ferritin, heavy polypeptide 1 |
| FYB | 2533 | FYN binding protein (FYB-120/130) |
| GPR34 | 2857 | G protein-coupled receptor 34 |
| GZMA | 3001 | granzyme A (granzyme 1, cytotoxic T-lymphocyte-associated serine esterase 3) |
| HBA1 | 3039 | hemoglobin, alpha 1 |
| HBA2 | 3040 | hemoglobin, alpha 2 |
| HBB | 3043 | hemoglobin, beta |
| HCK | 3055 | hemopoietic cell kinase |
| HCLS1 | 3059 | hematopoietic cell-specific Lyn substrate 1 |
| HHEX | 3087 | hematopoietically expressed homeobox |
| ICK | 22858 | intestinal cell (MAK-like) kinase |
| IL10RA | 3587 | interleukin 10 receptor, alpha |
| IL7R | 3575 | interleukin 7 receptor |
| IRF8 | 3394 | interferon regulatory factor 8 |
| ITGAM | 3684 | integrin, alpha M (complement component 3 receptor 3 subunit) |
| ITGAX | 3687 | integrin, alpha X (complement component 3 receptor 4 subunit) |
| LAIR1 | 3903 | leukocyte-associated immunoglobulin-like receptor 1 |
| LCP1 | 3936 | lymphocyte cytosolic protein 1 (L-plastin) |
| LGMN | 5641 | legumain |
| LILRA2 | 11027 | leukocyte immunoglobulin-like receptor, subfamily A (with TM domain), member 2 |
| LILRA4 | 23547 | leukocyte immunoglobulin-like receptor, subfamily A (with TM domain), member 4 |
| LILRB4 | 11006 | leukocyte immunoglobulin-like receptor, subfamily B (with TM and ITIM domains), member 4 |
| LOC283713 | 283713 | hypothetical protein LOC283713 |
| LPXN | 9404 | leupaxin |
| LTB | 4050 | lymphotoxin beta (TNF superfamily, member 3) |
| MAG | 4099 | myelin associated glycoprotein |
| MBP | 4155 | myelin basic protein |
| MDM2 | 4193 | Mdm2 p53 binding protein homolog (mouse) |
| MEI1 | 150365 | meiosis inhibitor 1 |
| METTL10 | 399818 | methyltransferase like 10 |
| MITF | 4286 | microphthalmia-associated transcription factor |
| MS4A14 | 84689 | membrane-spanning 4-domains, subfamily A, member 14 |
| MYL4 | 4635 | myosin, light chain 4, alkali; atrial, embryonic |
| NLRC4 | 58484 | NLR family, CARD domain containing 4 |
| NUP50 | 10762 | nucleoporin 50 kDa |
| P2RY12 | 64805 | purinergic receptor P2Y, G-protein coupled, 12 |
| PAQR5 | 54852 | progestin and adipoQ receptor family member V |
| PARP8 | 79668 | poly (ADP-ribose) polymerase family, member 8 |
| PDE4A | 5141 | phosphodiesterase 4A, cAMP-specific (phosphodiesterase E2 dunce homolog, *Drosophila*) |
| PFKFB3 | 5209 | 6-phosphofructo-2-kinase/fructose-2,6-biphosphatase 3 |
| PIK3CG | 5294 | phosphoinositide-3-kinase, catalytic, gamma polypeptide |
| PIK3IP1 | 113791 | phosphoinositide-3-kinase interacting protein 1 |
| PIP3-E | 26034 | phosphoinositide-binding protein PIP3-E |
| PIP4K2A | 5305 | phosphatidylinositol-5-phosphate 4-kinase, type II, alpha |
| PLAC8 | 51316 | placenta-specific 8 |
| PLEKHO2 | 80301 | pleckstrin homology domain containing, family O member 2 |
| PRPH2 | 5961 | peripherin 2 (retinal degeneration, slow) |
| PSCDBP | 9595 | pleckstrin homology, Sec7 and coiled-coil domains, binding protein |
| PTPN6 | 5777 | protein tyrosine phosphatase, non-receptor type 6 |
| QDPR | 5860 | quinoid dihydropteridine reductase |
| RABGEF1 | 27342 | RAB guanine nucleotide exchange factor (GEF) 1 |
| RCSD1 | 92241 | RCSD domain containing 1 |
| RHOF | 54509 | ras homolog gene family, member F (in filopodia) |
| RNASET2 | 8635 | ribonuclease T2 |
| SELPLG | 6404 | selectin P ligand |
| SEMA4D | 10507 | sema domain, immunoglobulin domain (Ig), transmembrane domain (TM) and short cytoplasmic domain, (semaphorin) 4D |
| SEPT4 | 5414 | septin 4 |
| SHISA4 | 149345 | shisa homolog 4 (*Xenopus laevis*) |
| SLA | 6503 | Src-like-adaptor |
| SLA2 | 84174 | Src-like-adaptor 2 |
| SLC17A5 | 26503 | solute carrier family 17 (anion/sugar transporter), member 5 |
| SLC2A5 | 6518 | solute carrier family 2 (facilitated glucose/fructose transporter), member 5 |
| SLC31A2 | 1318 | solute carrier family 31 (copper transporters), member 2 |
| SNCA | 6622 | synuclein, alpha (non A4 component of amyloid precursor) |
| STAT4 | 6775 | signal transducer and activator of transcription 4 |

TABLE 1-continued

List of 214 genes identified by subtractive analyses as GBM CD133 gene signature transcripts, with 89 elevated and 125 decreased in transcript levels in the CD133+ cells.

| | | |
|---|---|---|
| SUCNR1 | 56670 | succinate receptor 1 |
| SUSD3 | 203328 | sushi domain containing 3 |
| TAGAP | 117289 | T-cell activation RhoGTPase activating protein |
| TAX1BP1 | 8887 | Tax 1 (human T-cell leukemia virus type I) binding protein 1 |
| TFEC | 22797 | transcription factor EC |
| TLR2 | 7097 | toll-like receptor 2 |
| TLR7 | 51284 | toll-like receptor 7 |
| TLR8 | 51311 | toll-like receptor 8 |
| TNFRSF10C | 8794 | tumor necrosis factor receptor superfamily, member 10c, decoy without an intracellular domain |
| TNFRSF9 | 3604 | tumor necrosis factor receptor superfamily, member 9 |
| UNC84B | 25777 | unc-84 homolog B (*C. elegans*) |
| WNT2 | 7472 | wingless-type MMTV integration site family member 2 |
| XCL1 | 6375 | chemokine (C motif) ligand 1 |

Because it has been demonstrated below that the expression patterns associated with CD133+ cells are indeed characteristic of undifferentiated embryonic stem cell patterns, the signatures obtained from patient (human subject or veterinary subject) samples (or subject samples in laboratory studies) can be used to assess the grade of cancer in said subject. The more closely the signature matches the signature of up- and down-regulation of the CD133+ cells, the higher the cancer grade.

Thus, to assess the grade of cancer in a subject, a tumor sample is obtained by biopsy and mRNA extracted and applied to standard microarray analysis. Various methods of mRNA extraction and microarray analysis are known and commercially available. The resulting pattern of expression is then treated statistically according to the method of Setlur cited above or by any other statistical means that can be used to assess over- or under-expression of all of the genes in each of the up and down group in the sample and compared to the pattern for the genes in the CD133+ signature.

By the "grade" of cancer is meant the degree of severity; standard grade levels have been assigned to various cancers as is understood in the art.

The following examples are intended to illustrate but not to limit the invention.

PREPARATION A

Isolation of CD133+ and CD133− Cells

GBM samples were stored in sterile saline buffer and processed within 1-2 hours after resection. Tumors were cut into small pieces (~1-3 mm$^3$) and incubated with 1 mg/ml collagenase IV in NeuroCult™ NS-A media (StemCell Technologies) at room temperature overnight. The dissociated cells were filtered with 70 µM cell strainer, washed with HBSS; and then labeled with PE-conjugated CD133 antibody (Miltenyi Biotec, Inc), along with isotype control. CD133 positive and negative cells were sorted with BD Influx™ cell sorter.

Total RNA was extracted from both population with RNeasy™ kit.

The RNA was then applied to microarray analysis to obtain gene expression profiles.

The Wilcoxon rank-sum test was applied to the microarray data with a cutoff p value of 0.05. Genes exhibiting at least a two-fold difference between CD133+ and CD133− cells were chosen. Lower abundance genes, which showed the sum of all expression values below an arbitrary value set at 10 were removed from the list to obtain the 214 most differentially expressed genes set forth in Table 1 above. Of these, the "up" subset includes 89 transcripts that were elevated in the CD133+ population and a "down" subset which comprises 125 transcripts whose levels were decreased.

EXAMPLE 1

Correlation of Signatures with Patient Samples

Samples of glioblastoma (GBM) were obtained from five patients and sorted as described above into CD133+ and CD133− subpopulations. To compare the signatures in these samples to the signature obtained in Preparation A, the algorithm of Setlur, set forth above, was employed. As noted above, P=0=overexpression (indicated in the figures in red); P=0.5=normal expression (indicated in the figures in black); and P=1=underexpression (indicated in the figures in green).

Figure 1:
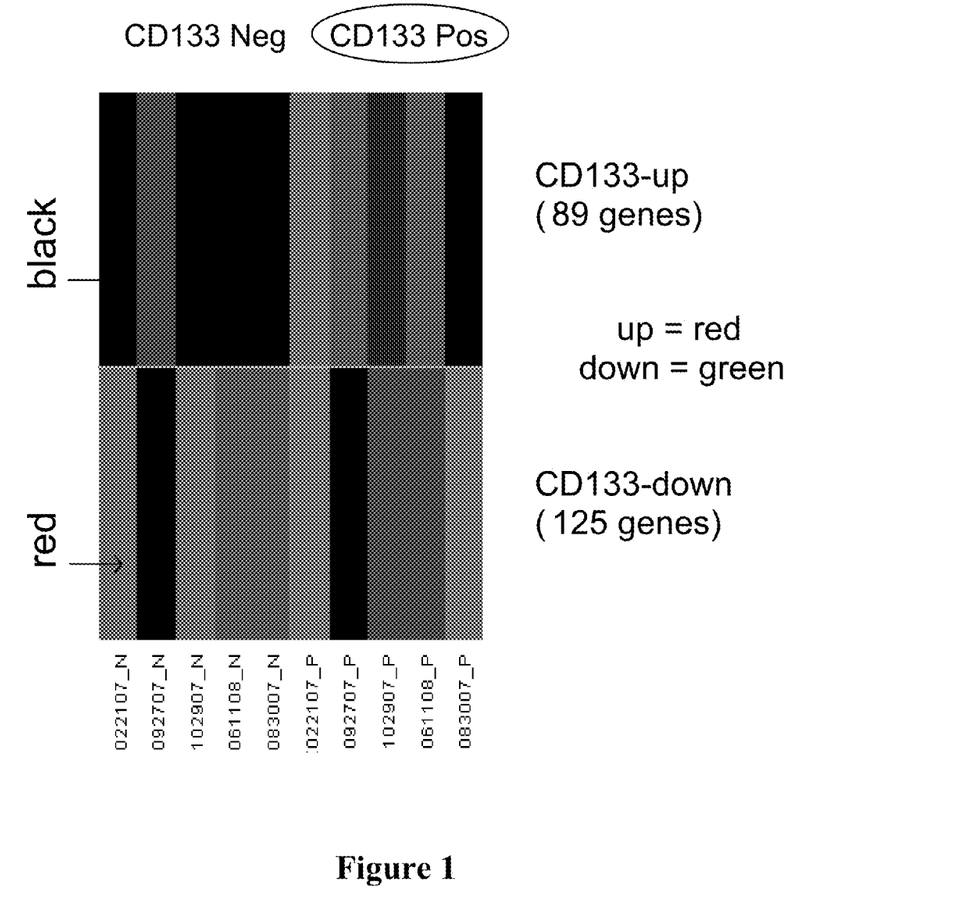
FIG. 1 shows the expression patterns of the CD133-up (89 genes) and CD133-down (125 genes) signatures in CD133$^+$ vs. CD133$^-$ cell populations isolated from five glioblastoma (GBM) patients. Each line in the heat map represents a P value for overexpression (red) or underexpression (green) of the given signature calculated from 10$^6$ computational iterations.

As shown in FIG. 1, individual patient profiles correlated reasonably well with the initial results in Preparation A. The CD133+ cells obtained from these patients in general showed overexpression of the expected genes and underexpression of the genes expected to be underexpressed. The CD133− cells from these patients showed the opposite expression pattern, i.e., underexpression of the CD133-up signature and overexpression of the CD133-down signature.

EXAMPLE 2

Correlation with Stem Cell Signatures

Microarray data from duplicate samples of human embryonic stem cell cultures were obtained from published dataset (Skottman, H., et al., *Stem Cells* (2005) 23:1343-1356). Expression levels of many genes, not just the 214 in Table 1 were disclosed. Upon applying the statistical analysis described in Example 1, the results in FIG. 2 were obtained.

Figure 2:
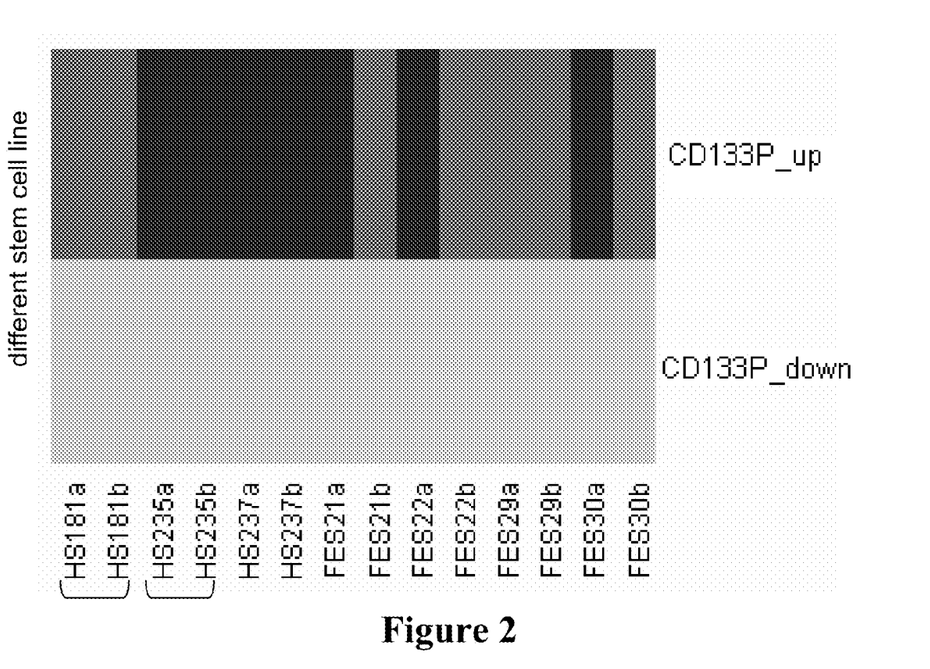
FIG. 2 shows the heat map of P values for expression patterns of the 89 up/125 down signatures in seven replicate stem cell cultures as related to the patterns in CD133$^+$ cells.

As shown, there is a substantially perfect correlation between the underexpressed genes in the stem cell population as compared to CD133 positive cell-down signature and a reasonably good correlation to the expression levels of genes that were up-regulated in the stem cells as compared to the CD133-up signature; confirming the stem cell nature of CD133+ cells.

In addition, the transcriptional relationship between neural stem cells (NSC) and primary glioblastoma (GBM) total cells cultured either in NSC-enriching medium or regular serum medium were compared. Microarray data for the GBM cells were obtained from published results of Lee, J., et al. (*Cancer Cell* (2006) 9:391-403).

In addition, cell samples from GBM patients were cultured in medium that maintains undifferentiated status, i.e., Neurobasal™ media supplemented with basic FGF and EGF (NBE medium) and medium that permits differentiation, i.e. standard serum-based medium. The expression profiles of
- 22 serum cultured GBM samples,
- 28 NBE media cultured GBM samples and
- three neural stem cell samples were compared. The statistics applied were Ward's minimum variance method as a clustering algorithm and Pearson correlation as a distance function. The CD133+ down gene set was used as a clustering feature.

Figure 3:
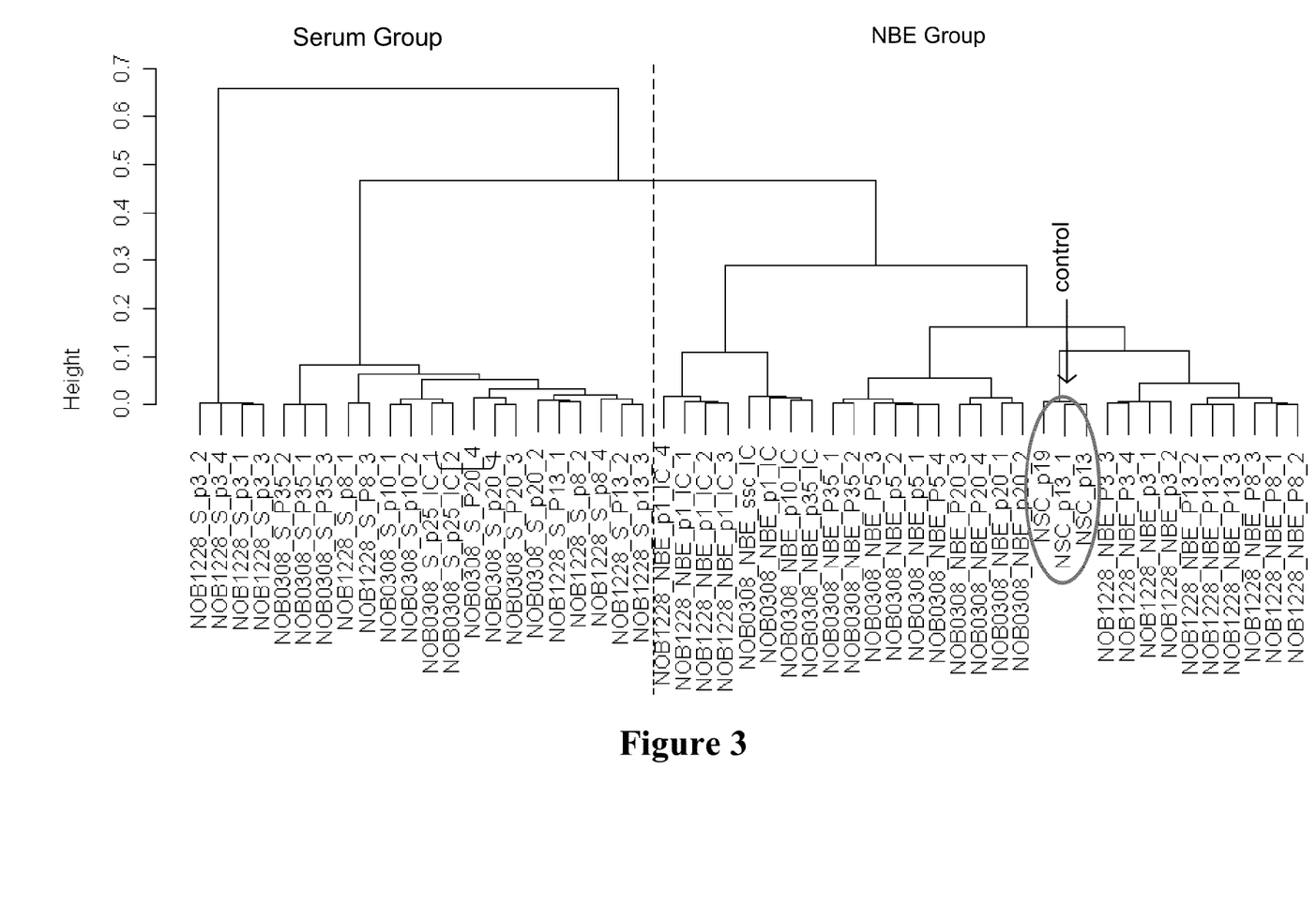
FIG. 3 shows the clustering of gene expression profiles of primary GBM samples either cultured in serum-containing medium which encourages differentiation or stem cell enriching medium, which maintains undifferentiated status.

FIG. 3 shows the results. Each data point represents a different cell culture. As shown, the expression pattern of the NBE group separated from the serum group, and the neuronal stem cells clearly reside within the NBE group. Thus, the NBE medium expands a stem cell-like population from the GBM tumor cells which bear an intrinsic correlation with freshly sorted CD133$^+$ populations.

EXAMPLE 3

Correlation of Signatures with Cancer Grade

Figure 4:
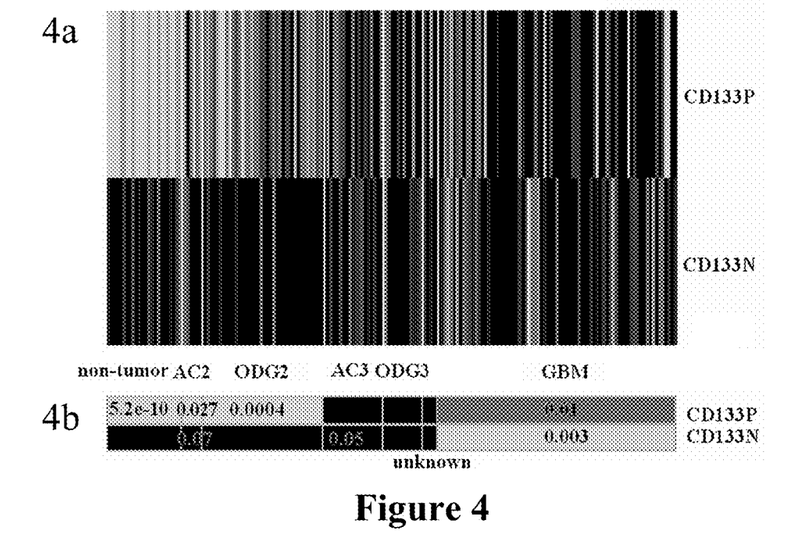
FIG. 4a is a heat map of P value, wherein each vertical line represents a patient sample grouped according to histopathological stages, labeled as non-tumor (control), AC2 (grade 2 astrocytoma), ODG2 (grade 2 oligodendroglioma), AC3 (grade 3 astrocytoma), ODG3 (grade 3 oligodendroglioma), and GBM (grade 4 astrocytoma).
FIG. 4b shows the P values of over- or underexpression for each subgroup of patients calculated according to the hypergeometric distribution.

Microarray data from normal subjects and from subjects who had been diagnosed at various World Health Organization (WHO) grade levels of glioma were obtained from published results (Sun, L., et al., *Cancer Cell*. (2006) 9:287-300.) These data included expression levels for many genes, not just the 214 genes included in Table 1. All cells were included, not separated into CD133$^+$ and CD133$^-$. The dataset included 181 brain samples and statistical analysis was applied to the signatures as described above. The results are shown in FIG. 4 for these 181 subjects.

As shown, in the non-tumor samples and those of lower grades (AC2 and ODG2) strong correlations with the up and down profile determined herein for CD133-negative cells is observed in the samples. For subjects with medium grade AC3 ODG3 gliomas essentially no correlation exists over the population. A good correlation with the up and down profile determined herein for CD133-positive cells exists for those with high grade tumors, i.e., grade 4 astrocytoma (GBM). As seen, the genes up-regulated in CD133$^+$ cells are up-regulated in these patients for the most part, and those that are down-regulated, are also downregulated in these samples. FIG. 4b also shows that a reasonable statistical test for the lack of glioma or very low grade glioma resides in demonstrating that genes overexpressed in CD133$^+$ are underexpressed in these tissues.

EXAMPLE 4

Correlation with GBM Subpopulations

Figure 5:
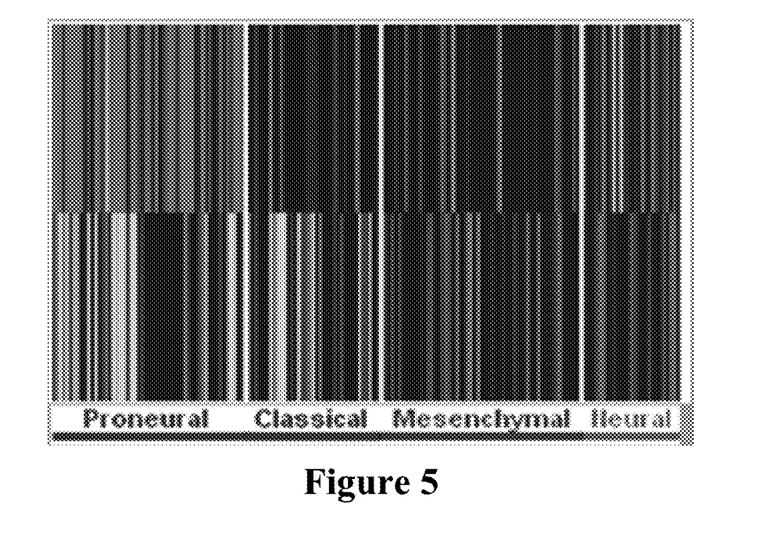
FIG. 5 shows the enrichment pattern of the CD133 gene signatures in different GBM molecular subtypes: Proneural, Classical, Mesenchymal, and Neural. Probabilistic values for gene-set enrichment are used to draw the heat map: red, enrichment for overexpression with probabilistic values toward 0; green, enrichment for underexpression with probabilistic values toward 1; black, no significant change, probabilistic values toward 0.5.

Heterogeneous GBM populations have been clustered into four molecular subtypes: Proneural, Neural, Classical, and Mesenchymal, based on gene expression profiles (Verhaak, R. G., et al., *Cancer Cell* (2010) 17:98-110, and Phillips, H. S., et al., *Cancer Cell* (2006) 9:157-173). The CD133 gene signatures were mapped onto the four molecular subgroups defined by The Cancer Genome Atlas (TCGA) network with a total of 173 patients. The most prominent enrichment occurs in the Proneural cluster with diminishing appearance in other subtypes. This is shown in FIG. 5. It has been reported that the Proneural cluster demonstrated unresponsiveness to a more intensive treatment regime as opposed to the other clusters, and a general trend (statistically non-significant) toward longer survival. (Verhaak, et al., supra.)

EXAMPLE 5

Alternative Classification

The 173 TCGA patient GBM samples of Example 4 were reclassified into three classes as follows:
1) The CD133-active class (43 patients): either of the two signatures (CD133 positive or CD133 negative) supports the activation of CD133 while the other one does not oppose it;
2) The CD133-inactive class (16 patients): either of the two signatures supports the inactivation of CD133 while the other one does not oppose it;
3) The CD133-semi-active class (114 patients): all remaining patients that fall outside of classes 1 and 2.

The clinical relevance of these new GBM classes was correlated with reported patient outcomes from the TCGA data. The CD133-active class contains more younger patients, but, in contrast to the Proneural subtype who survive longer (Verhaak, et al., supra), these patients exhibited shorter survival when compared to the CD133-inactive class. The most significant patient group appears at age 45 or younger, with a survival of 362 days or less. This was validated in two additional datasets using survival curves (Philips, et al., supra; Murat, A., et al., *J. Clin. Oncol.* (2008) 26:3015-3024).

Figure 6:
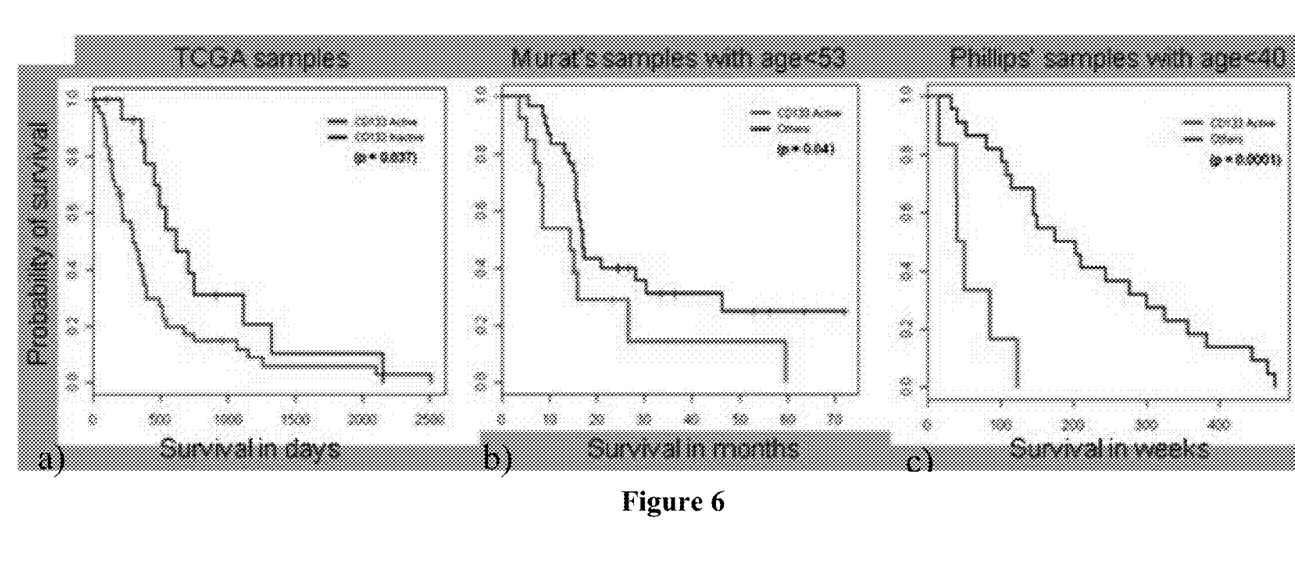
FIGS. 6a, 6b and 6c show survival curves of CD133 active vs CD133 inactive/others in three independent GBM datasets.

The CD133-active class showed much shorter survival than the rest of patients in both datasets as shown in FIG. 6. Thus, the CD133 signature identifies a younger but more aggressive subtype within GBM.

EXAMPLE 6

Genetic Correlation

Figure 7:
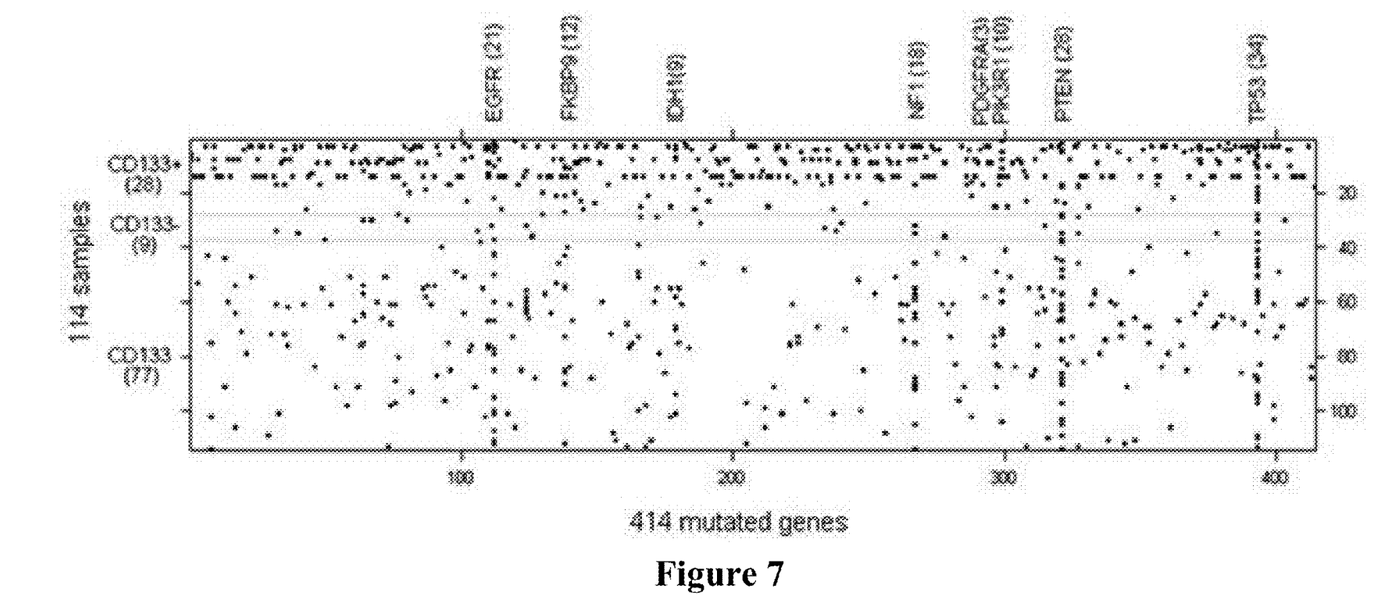
FIG. 7 shows distribution of genomic mutations among three CD133 classes of GBM patients. Mutation and gene expression data were obtained from published TCGA datasets.

The genomic abnormalities underlying the three CD133 GBM subclasses in Example 5 were determined. A total of 747 mutations on 414 genes in 114 patient samples in these groups were detected through exam sequencing by TCGA. The CD133-active class with only 28 patients (25% total with mutation data available) accounts for more than half (399/747) of all the mutations identified. The average mutation rate per patient is 4 and 3 times greater than the CD133-inactive and semi-active classes respectively. The distribution of all gene mutations among the three CD133 GBM classes with frequently mutated genes highlighted (e.g., EGFR, IDH1, NF1, PDGFR, PTEN, and TP53) is illustrated in FIG. 7. Although the majority of mutations occur in the phenotypically aggressive CD133-active subtype, no particular mutation pattern of any specific genes across the three subtypes are observed, suggesting that combinatorial stochastic (as opposed to a peculiar) genetic aberrations, contribute, in a quantitative manner, to the tumorigenic properties of cancer stem cells.

EXAMPLE 7

Breast Cancer Samples

Figure 8:
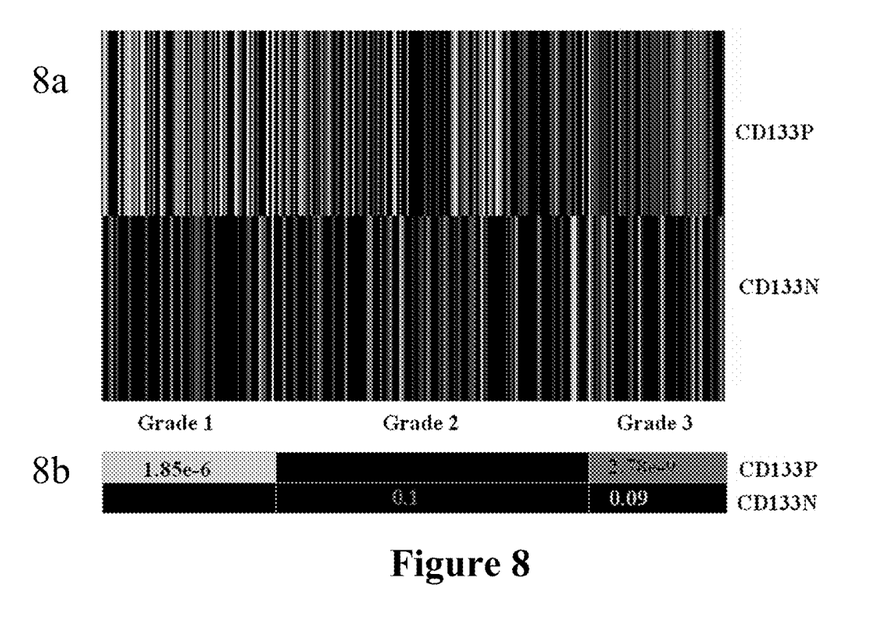
FIGS. 8a-b show results similar to those in FIGS. 4a-b in samples from individuals with different grades of breast cancer.

Similar results to those in Example 3 for GBM were obtained in 189 breast cancer samples as shown in FIG. 8. These results were compared to the results gene profiling using alternative procedures described by Sotiriou, C., et al., *J. Natl. Cancer Inst.* (2006) 98:262-272. One hundred and fifty-seven (157) bladder cancer profiles were also assessed and the results compared with the results of Sanchez-Carbayo, M., et al., *J. Clin. Oncol.* (2006) 24:778-789, showing similar correlations.

The invention claimed is:
1. A method to assess the grade of a tumor in a subject, which method comprises
 (a) providing a sample containing tumor cells from the subject,
 (b) assessing the expression signature in the cells in said sample of at least 10 genes selected from among those in Table 1, and
 (c) assessing the expression signature of said at least 10 genes in CD133$^+$ vs. CD133$^-$cells,
 (d) comparing the resulting expression signature determined in (b) with the expression signature in (c), wherein a statistically significant correlation of the expression signature in (b) as compared to the expression signature in (c) indicates a high grade tumor, wherein said expression signatures are assessed by measuring mRNA levels.

2. The method of claim 1 wherein said assessing, comparing and correlating is of at least 20 genes from among the genes listed in Table 1.

3. The method of claim 2 wherein said assessing, comparing and correlating is of at least 50 genes from among the genes listed in Table 1.

4. The method of claim 3 wherein said assessing, comparing and correlating is of at least 70 genes from among the genes listed in Table 1.

5. The method of claim 1 wherein said tumor is breast tumor, bladder tumor or glioma.

* * * * *